(12) United States Patent
Saketkhou

(10) Patent No.: US 8,086,320 B2
(45) Date of Patent: Dec. 27, 2011

(54) WIRELESS COMMUNICATION DEVICE WITH INTEGRATED DEFIBRILLATOR

(76) Inventor: B. Benjamin Saketkhou, Boca Raton, FL (US)

( * ) Notice: Subject to any disclaimer, the term of this patent is extended or adjusted under 35 U.S.C. 154(b) by 88 days.

(21) Appl. No.: 12/541,739

(22) Filed: Aug. 14, 2009

(65) Prior Publication Data

US 2010/0042171 A1 Feb. 18, 2010

Related U.S. Application Data

(63) Continuation-in-part of application No. 11/438,233, filed on May 22, 2006, now abandoned.

(51) Int. Cl.
*A61N 1/08* (2006.01)
*A61N 1/24* (2006.01)
*A61N 1/362* (2006.01)
*A61N 1/378* (2006.01)

(52) U.S. Cl. .......... 607/60; 607/5; 607/30; 607/31; 607/32

(58) Field of Classification Search .......... 607/5, 30–32, 607/60
See application file for complete search history.

(56) References Cited

U.S. PATENT DOCUMENTS

| | | |
|---|---|---|
| 4,102,332 A | 7/1978 | Gessman |
| 4,531,527 A | 7/1985 | Reinhold, Jr. et al. |
| 5,078,134 A | 1/1992 | Heilman et al. |
| 5,228,449 A | 7/1993 | Christ et al. |
| 5,336,245 A | 8/1994 | Adams et al. |
| 5,544,661 A | 8/1996 | Davis et al. |
| 5,741,306 A | 4/1998 | Glegyak et al. |
| 5,782,878 A | 7/1998 | Morgan et al. |
| 6,041,255 A * | 3/2000 | Kroll .................. 607/5 |
| 6,408,206 B1 | 6/2002 | Kroll et al. |
| 6,580,908 B1 * | 6/2003 | Kroll et al. ............ 455/435.1 |
| 6,595,918 B2 | 7/2003 | Gopinathan et al. |
| 6,658,290 B1 | 12/2003 | Lin et al. |
| 6,747,556 B2 | 6/2004 | Medema et al. |
| 6,804,558 B2 | 10/2004 | Haller et al. |
| 7,072,712 B2 | 7/2006 | Kroll et al. |
| 2004/0019261 A1 | 1/2004 | Gopinathan et al. |
| 2004/0027245 A1 | 2/2004 | Schlager et al. |
| 2006/0009684 A1 | 1/2006 | Kim |

OTHER PUBLICATIONS

"Saving Lives—Cell Phone with Defibrillator (Gallery)" in Trendhunter Magazine, www.trendhunter.com/trents/saving-lives-cell-phone-with-defibrillator (printed Mar. 25, 2009).
"Automated External Defibrillator AED and Cabinets", www.911phone.net/aed.htm (printed Mar. 25, 2009).
"High-Tech Defibrillators Save Lives", wbztv.com/local/CBS4.Boston.High.2.572841.html (printed Mar. 25, 2009).
"Physio-Control: Defibrillator/Monitors", www.voicesoflifesaving.com/products/defib.htm (printed Mar. 25, 2009).

(Continued)

*Primary Examiner* — Carl H Layno
*Assistant Examiner* — Natasha Patel
(74) *Attorney, Agent, or Firm* — McHale & Slavin, P.A.

(57) ABSTRACT

A handheld wireless communication device having a defibrillator integrated therein to be employed in an emergency situation to supply electrical therapy to a victim who is experiencing cardiac distress. The defibrillator being powered by at least one thermally powered battery contained within the wireless communications device. The wireless communication device may also include a cardiac module which will determine whether the victim's heart beat has become irregular and whether defibrillation is necessary. The wireless communication device will guide the user through the use of the defibrillator/cardiac modules. The wireless device may also include a tracking unit that will provide the user's location and wireless two-way voice communication with emergency personnel upon activation of the defibrillator.

13 Claims, 3 Drawing Sheets

OTHER PUBLICATIONS

"Is wi-fi making me sick?/Defibrillator with SiFi Option/Wireless warning sounded", weepnews.blogspot.com/2008/12/is-wi-fi-making-me-sick-defibrillator.html (printed Mar. 25, 2009).

"Security Information for the LIFEPAK 12 Defibrillator/Monitor Series" Medtronic, www.physio-control.com (2007).

* cited by examiner

WIRELESS COMMUNICATION DEVICE WITH INTEGRATED DEFIBRILLATOR

CROSS REFERENCE TO RELATED APPLICATIONS

This application is a continuation-in-part of application Ser. No. 11/438,233, entitled Wireless Communication Device with Integrated Defibrillator, filed on May 22, 2006, now abandoned the entire contents of which is hereby expressly incorporated by reference.

FIELD OF THE INVENTION

The invention generally relates to a handheld portable wireless communication device. In particular, toward a cellular telephone with a defibrillator integrated therein capable of delivering an electrical charge to defibrillate the heart of a victim experiencing cardiac distress. The cellular phone and integrated defibrillator uses a thermal battery which provides the necessary power density to enable practical portability of the device.

BACKGROUND OF THE INVENTION

Sudden cardiac death (SCD) occurs in approximately 400,000 people in the U.S. each year. Half of all coronary heart disease deaths are sudden and unexpected; these include people at risk of dying from SCD while they are awaiting a heart transplant or immediately after they survive a heart attack. SCD is a direct result of cardiac arrhythmia (cardiac arrest) and may be reversible if responded to promptly through the administration of at least one electrical shock to the victim's heart. If left uncorrected, the irregular heartbeat can lead to irreversible brain damage and even death. It has been determined by the American Heart Association that for every minute that a person experiences cardiac arrhythmia without being defibrillated, the chance of survival decreases by about 10 percent.

Defibrillators have been used for years to restore normal heart rhythm to victims experiencing cardiac arrhythmia, these include external and implantable defibrillators. However, those patients who typically benefit from such implantable defibrillators face an increased risk of complications resulting from the implantation surgery. Thus, these patients are usually confined to extended hospitalization so that they may receive prompt defibrillation, if necessary. Doctors sometimes recommend home defibrillators for patients with chronic heart conditions (e.g., heart disease).

Portable external defibrillators have been in use for years and depend on bystanders to successfully administer the electrical therapy to the victim. Recently the U.S. Food and Drug Administration approved the use of a wearable cardioverter defibrillator available from Lifecor, Inc. (Pittsburgh, Pa.), see U.S. Pat. No. 5,741,306. This defibrillator is strapped to the lower chest and shoulders of the user and must be continuously worn in order to detect and impart electrical therapy in response to cardiac arrhythmia in the patient. However, this wearable defibrillator is bulky and cumbersome, reducing the likelihood the user will continuously wear the device, thereby decreasing its effectiveness.

A basic defibrillator consists of a power source (i.e., battery), microprocessor, and electrodes interconnected by electrical circuitry. The defibrillator can include a cardiac module which utilizes the same or different electrodes than the defibrillator. These electrodes sense the heart's rhythm and the microprocessor interprets the rhythm to determine if a shock is needed to treat fibrillation. If the heart is in fibrillation, the defibrillator will charge in preparation to deliver the shock. The electrodes deliver an electric shock that travels through the victim's chest to stun the heart, momentarily stopping all activity. This momentary inactivity gives the heart a chance to restart normal electrical activity and resume beating. A successful defibrillation is one that causes the fibrillation to be converted to another rhythm, even if this rhythm is unshockable.

Public automated external defibrillators (AEDs) have been in use for years. Most AEDs have been designed to require little to no training to operate. These AEDs are found in public places where groups of people congregate, such as, offices, airports, restaurants, hotels, schools, etc. Public AEDs are usually mounted inside brightly colored, protective cases to make them highly visible to the community. When these protective cases are opened and defibrillator removed, often an alarm will indicate their removal. However, most of these alarms do not summon emergency services and only some AEDs include a phone to contact emergency personnel. Those AEDs that do include a telephone depend upon fact that the person making the call is aware, or capable, of determining the exact location of the victim.

There are two types of automated external defibrillators: semi-automatic and fully-automatic. Both types approved in the United State will prompt and guide the operator through the use procedures visually, audibly or both. The semi-automatic AEDs will instruct the operator to stand clear of the victim and to push a shock button to defibrillate. The fully-automatic units will warn the operator to stand clear and then deliver the shock automatically without the user having to push a button.

Wireless communication devices (cellular telephones, PCS, personal digital assistants, pagers, etc.) have become virtually ubiquitous in many societies. These wireless devices are currently being developed for use over a wide swath of health care applications. These include, albeit not limited to, patient monitoring, equipment monitoring, telemedicine, prescriptions and patient record keeping. Given their ready accessibility it makes sense to integrate these wireless communication devices with equipment capable of providing emergency medical capabilities.

What has been heretofore lacking in the art is a wireless telecommunication device capable of normal everyday communication which is also capable of recognizing a cardiac irregularity and, if deemed necessary, defibrillates the victim. The present invention is particularly ideal for patients at risk for sudden cardiac arrest and those who are not candidates or refuse an implantable defibrillator. The device utilizes a power supply that can retain a sufficient amount of electrical energy to power the defibrillator yet is small enough in both size and weight to be easily carried on one's person or inside a handbag.

DESCRIPTION OF THE PRIOR ART

Numerous patents have been directed to defibrillators with various means to provide accurate information to remotely located emergency personnel, some of these include a Global Positioning System (hereinafter, GPS), communication device, diagnostic devices and algorithms, etc. None of the known prior art discloses a conventional wireless communication device (e.g., cellular phone) capable of providing automatic defibrillation during the occurrence of a cardiac condition.

For example, U.S. Patent Application Publication No. 2004/0027245 A1, to Schlager et al., incorporates a separate satellite global positioning receiver and a radio transmitter into a modified smart defibrillator. The defibrillator is modified so that the detection of an irregular heart rhythm provides a signal for activating the radio transmitter for transmitting the global location to a base receiver, typically located in an emergency room. In a specific embodiment, the satellite global receiver relies upon the GPS and the radio transmitter is provided by a separate wireless telephone.

U.S. Patent Application Publication No. 2004/0019261 A1 and U.S. Pat. No. 6,595,918, B2, both to Gopinathan et al., disclose a system for collecting a variety of diagnostic information and transmitting the diagnostic information to a remote location and providing emergency treatment. The system comprises a first member and a second member worn on the emergency personnel's hands (e.g., doctor). These members comprise a plurality of diagnostic devices and a defibrillator device. The system includes a transmitting unit for transmitting information to, and receiving information from, a remote location.

U.S. Pat. No. 6,747,556 B2 to Medema et al discloses a method and system for locating a portable medical device. The invention provides a wireless automatic location identification (ALI) capable system, including a medical device having a wireless communicator, a wireless communication network and a remote locating service for remotely locating and monitoring one or more medical devices over the wireless communication network. When the medical device is linked to the remote location service over the communication network, the ALI-capable system identifies the location of the medical device and relays the location information to the remote locating service. While this reference does contemplate a medical device (i.e., defibrillator) that integrally incorporates the data communicator, the reference does not teach or suggest the use of a wireless data communicator capable of normal everyday communication that can be used as a defibrillator during cardiac emergencies. That is, the data transferred and received from the data communicator in the '566 patent relates only to requested status or condition information, self-test results, physiological data related to patient, and is not designed for normal everyday use as a wireless communication device.

U.S. Pat. No. 6,658,290 B1, to Lin et al. discloses a public accessible defibrillator which includes a detector used to detect a life threatening condition of a patient, a controller operating the defibrillator automatically and a therapy delivery circuit that delivers appropriate therapy. The defibrillator is attached to a patient by any attendant or bystander and once it is attached, the defibrillator is adapted to monitor the patient and when a life threatening condition is detected, to apply therapy automatically, i.e., without any involvement by the patient or the attendant. A communication module may be also be provided within the defibrillator to alert personnel at a remote location that the patient has experienced a life threatening episode and that therapy is being delivered by the automatic defibrillator. Emergency personnel (such as an ambulance) may be dispatched to provide assistance. The communication module may include a locator unit, such as GPS, which provides the physical location of the patient. The communication module may make use of a cellular telephone system, wireless radio, telephone system, a controller network, the Internet, and the like.

U.S. Pat. Nos. 6,041,255 and 6,408,206, to Kroll and Kroll et al, respectively, disclose a disposable external defibrillator, the contents of each of these two patents is hereby expressly incorporated by reference. These patents disclose a pocket-sized disposable external defibrillator that relies on the use of a thermal battery. The thermal battery uses a pyrotechnic molten salt electrolyte that delivers an extremely high current for a short period of time thus providing an energy source for an external disposable defibrillator.

U.S. Pat. No. 7,072,712, to Kroll et al discloses a disposable cardiac defibrillator that relies on the use of a split unit packaging design to decrease the overall size of the device, the contents of which is hereby expressly incorporated by reference. The device consists of two separate housing halves linked by a flexible link that is a hinged mechanism such that the two halves open like a book. One of the housing halves holds the thermal batteries and capacitors while the other halve holds the control circuit and monitoring battery.

SUMMARY OF THE INVENTION

Accordingly, the present invention is related to a handheld wireless communication device (e.g., cellular telephone) for sending and receiving communication signals during normal operation. The present invention takes advantage of the fact that most people constantly carry some form of wireless communication (cellphone, pager, PDA, etc.) and that the wireless communicator can establish communications with remotely locate emergency personnel upon activation of the defibrillator module.

It is an objective of the instant invention to provide a wireless communication device that includes a cardiac module capable of determining whether the victim's heart beat has become irregular, whether defibrillation is necessary and, if necessary, whether defibrillation was successful.

It is a further objective of the instant invention to provide a conventional wireless communication device that may have integrated therein at least one multimedia devices (camera, mp3 player, etc.)

Yet another objective of the instant invention to teach a wireless communication device including a tracking module capable of determining and automatically sending the location coordinates of the device to emergency personnel and/or the user interface of the wireless device so that the person making the call is able to determine the exact location of the victim.

Another objective of the present invention is to utilize the wireless E911 standard prescribed by the U.S. Federal Communications Commission that mandates cellular phone service providers supply the capability to locate the position of a cellular phone making an emergency (911) call.

Still a further objective of the invention to teach a wireless communication device including a defibrillator that will guide an operator with no medical training through the defibrillation process.

It is yet another objective of the invention is to teach a communication module capable of simultaneously contacting remotely located emergency personnel to obtain assistance for the victim.

It is yet another objective of the invention to teach a wireless communication device including a defibrillator and a source of electrical energy that is sufficient to power the defibrillator that has a size and weight that makes it readily transportable on one's person.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

The term defibrillation, as used herein, includes both cardioversion pulses and defibrillation pulses. Defibrillation pulses are generally asynchronous with respect to the cardiac electrical cycle, and cardioversion are generally synchronized with the cardiac cycle. These pulses include monophasic and/or biphasic shock waves.

The phrase emergency personnel, as used herein, refer to any trained person capable of providing emergency aid these include, albeit not limited to, persons in an emergency room, emergency clinic, paramedics, fire rescue, etc.

Figure 1:
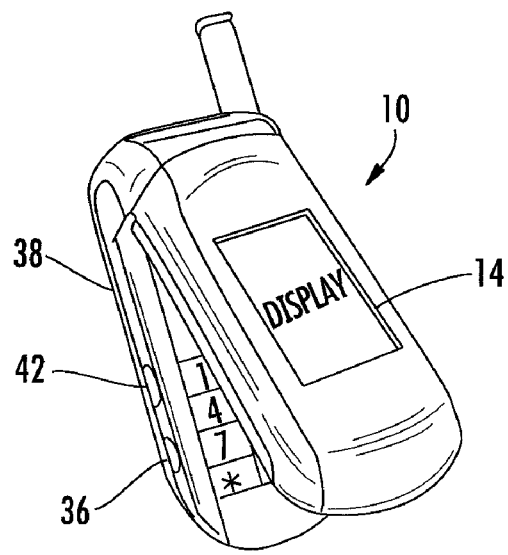
FIG. 1 is a perspective view of a partially open conventional clamshell-type cellular phone handset with a defibrillator module housed therein.
Figure 2:
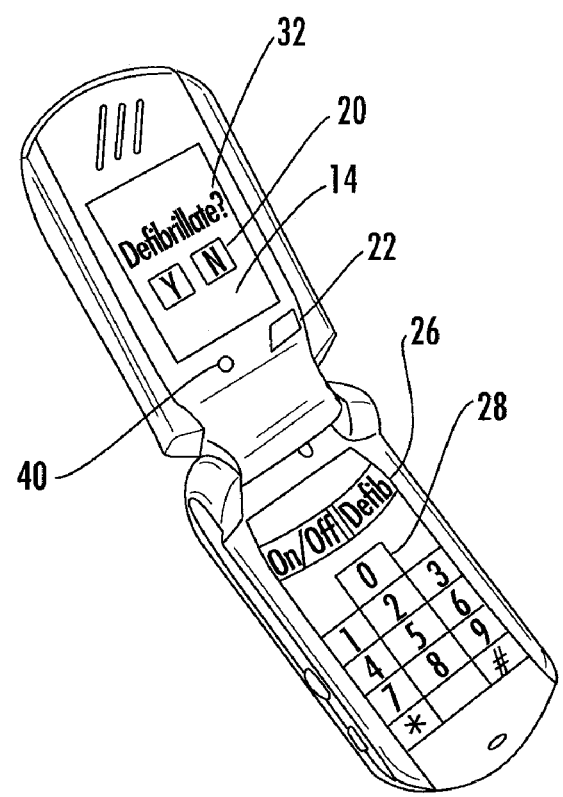
FIG. 2 is a perspective view of the cellular phone handset of FIG. 1 fully open, illustrating the defibrillator and cardiac module controls, electrodes and user display.

FIGS. 1 and 2 illustrate a standard clamshell type cell phone 10 capable of conventional wireless communication and which includes a defibrillator therein in accordance with the teachings of the present invention. It is hereby contemplated that other types, styles and models of wireless communication devices could be utilized without departing from the scope of the invention. Examples of other suitable types of wireless communication devices include, satellite telephones, pagers, personal data assistants, or a combination thereof.

Figure 3:
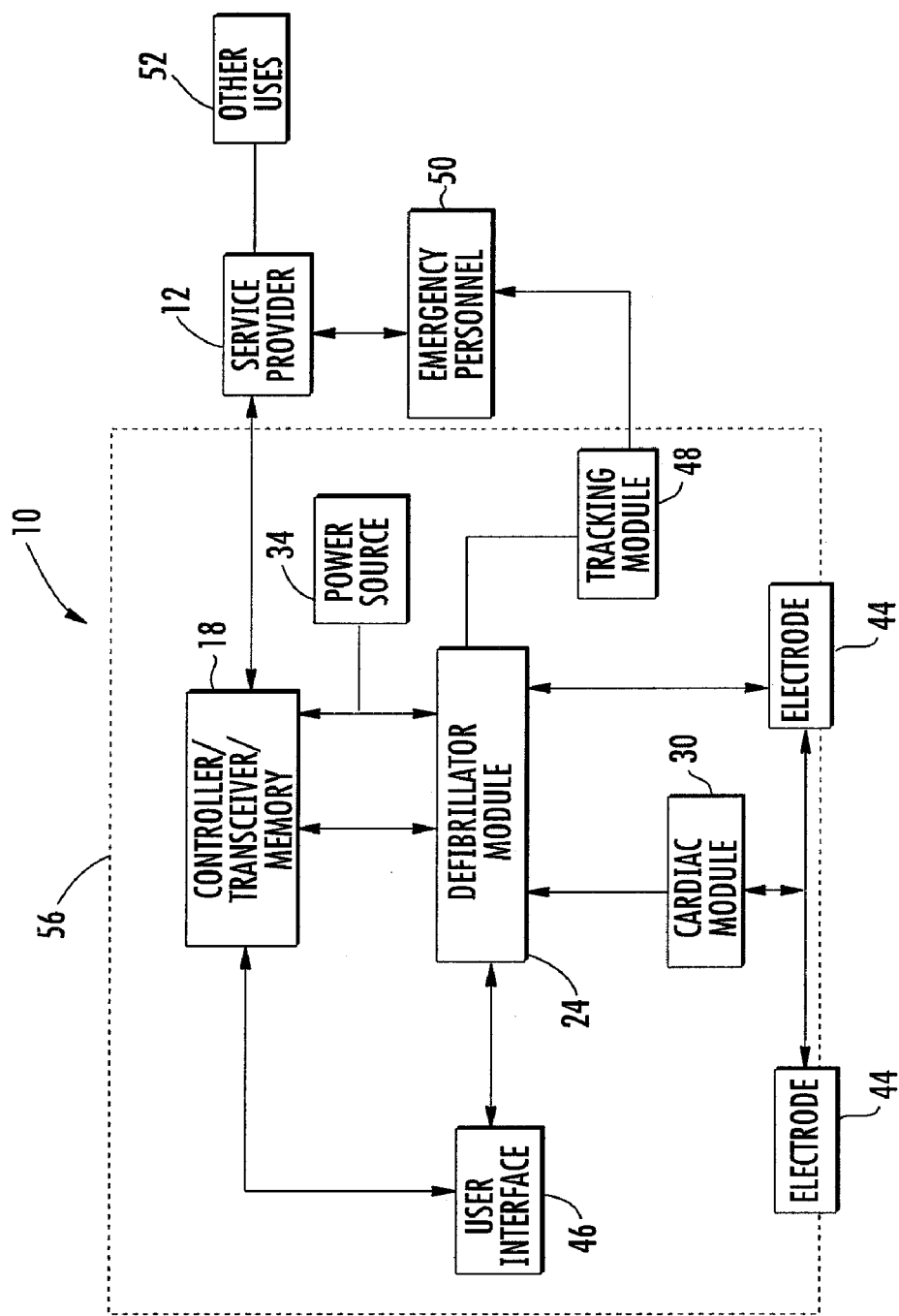
FIG. 3 a block diagram of a modified wireless communication device in accordance with the teachings of the present invention.

FIG. 3 is a block diagram illustrating a system for providing immediate emergency assistance to a person experiencing cardiac distress in accordance with one embodiment of the instant invention. The system includes a wireless communication device that communicates with a wireless service provider 12 as is known in the art.

Referring now to FIGS. 1-3, the wireless communication device includes a user interface 46 which includes a display 14, keypad 16, etc. in communication with a control unit 18 used to control the operation of the device. The control unit includes, at least, a transceiver, a microprocessor (not shown), memory, and power source. The display screen could be a touch screen with a standardized virtual keyboard or keypad on the display screen, whereby the user enters input commands via virtual buttons 20 displayed on the screen, as shown in FIG. 2.

The user interface may also include a speaker/microphone 22 that enables hands-free communication. This provides emergency personnel the ability communicate with individuals in close proximity to the wireless device without having to touch the device, this is particularly desirable during the operation of the defibrillator module 24, as discussed further below. The user interface should include at least one button (shock button) used to directly control the operation of the defibrillator and a cardiac module, shown here as buttons 26, 28, respectively.

The memory in the control unit can be used to store any software necessary to operate the device, the defibrillator module 24 and/or cardiac module 30. The software for the defibrillator should include stepwise instructions and prompts 32 designed to guide the operator through the delivery of the defibrillating shock (see FIG. 2). These instructions might include safety interlocks designed to prevent a user or operator from inadvertently getting shocked by defibrillator during use as a cellular telephone. The control unit should also enable the cellular phone to send and receive communication signals, such as voice, text messaging, Short Burst Data (SBD), pictures, video, or the like, with other users 52 (FIG. 3) as is common in everyday operation of wireless communication devices.

In one embodiment, the defibrillator module is capable of operating in various modes (e.g., automatic, semi-automatic) that the user can select via the user interface. For example, in fully automatic mode the wireless device instructs the operator to stand clear and then delivers the shock without the user having to push a button. In the semi-automatic mode the device will instruct the operator to push a shock button to initiate the defibrillation and then stand clear of the victim.

Referring now to FIG. 3, the wireless device includes a power source 34 used to supply power to each individual module in the device. The power source may be supplied directly from an outside source, such as, a 110-voltage wall outlet via power cord via a power connection port 36 (FIG. 1) located on the exterior of the housing 38. However, for enhanced mobility it is preferred that the wireless communication device includes at least one portable power source housed on the exterior or inside the wireless device. One non-limiting example of a portable power source includes rechargeable high density batteries (Lithium Ion) or the like.

Figure 4:
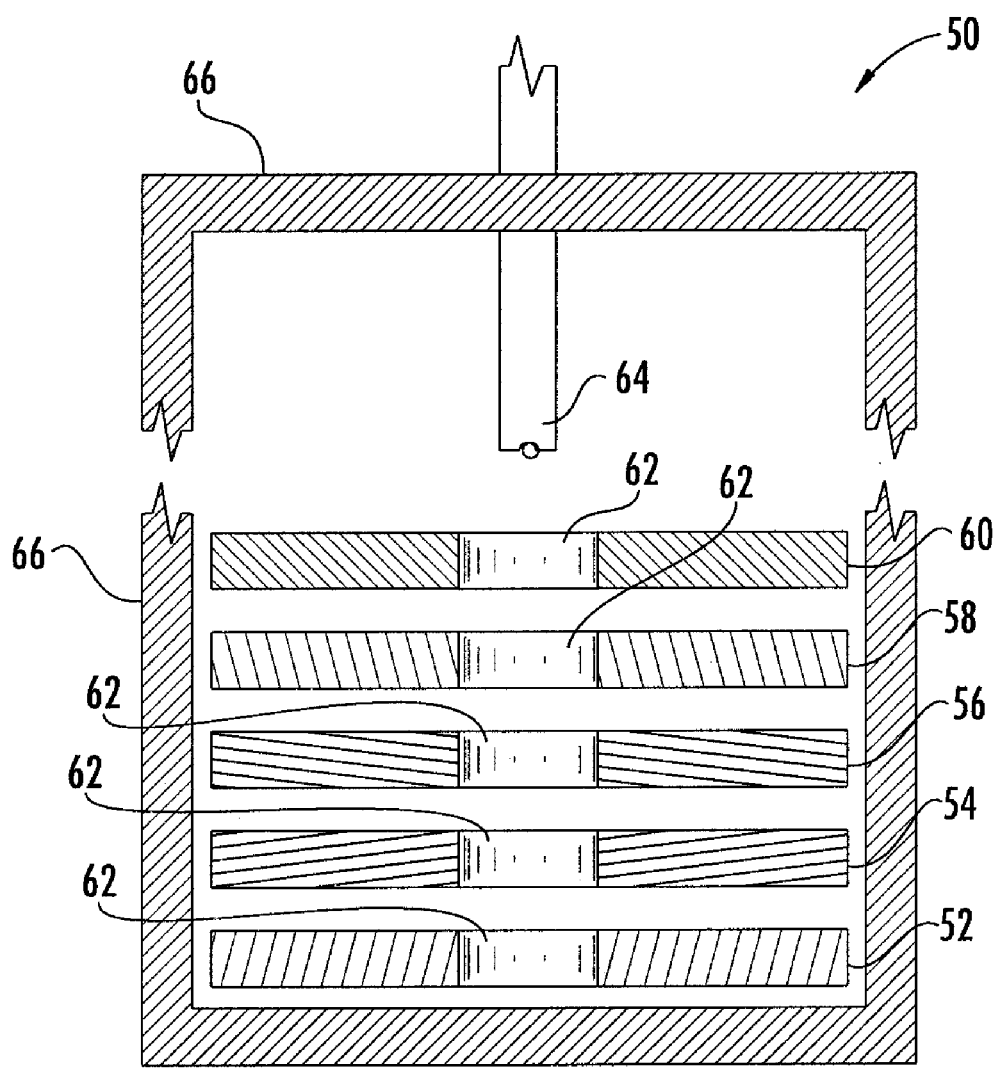
FIG. 4 is a schematic representation of the defibrillator thermal battery shown partially exploded and in section for clarity.

A preferred high density battery would be one such as the thermal battery illustrated in FIG. 4. Thermal batteries have been recognized primarily for use in missiles and artillery shells. As shown in the partially exploded sectional view of FIG. 4 the thermal battery 50 includes a pyrotechnic heat source 52, a cathode 54, and electrolyte 56, an anode 58 and a collector 60. The pyrotechnic heat source 52, the cathode 54, the electrolyte 56, the anode 58 and the collector 60 are formed as plates with a generally centrally located aperture 62. The anode can be made of lithium, calcium, magnesium, as well as other suitable material. The cathodes can be formed from a variety of materials such as $FeS_2$, $K_2Cr_2O_7$, $WO_3$, $CaCrO_4$, and $V_2O_5$ The pyrotechnic heat source 52 is formed from a combination of Fe and $KCLO_4$. The pyrotechnic heat source 52 can be ignited electrically by passing electricity through electrodes 64 positioned within the aperture of 62 of the plates. As the thermal reaction will reach relatively high temperatures the material is encapsulated in thermal insulation 66. Multiple thermal batteries may be employed to provide additional power to the defibrillator. The amount of energy stored in a thermal battery per unit volume of space and weight is substantially higher than a conventional battery. The battery or batteries can be sized and configured to be housed within the wireless communication device or may be formed as a power pack separate from the wireless device. Alternatively, the device may have one thermal battery housed within the wireless device and an additional or supplemental thermal battery may be provided external to the wireless device with the appropriate electrical connector.

The wireless communication device may also include at least one multimedia device therein, each in communication with the control unit. Examples of suitable multimedia device include, albeit not limited to, a camera unit (lens 40, FIG. 2), frame grabber (not shown), MP3 player (not shown), or the like. Moreover, the wireless communication device may also include at least one data connection port 42 (FIG. 1), wherein each port provides connection to an external device capable of transferring data to and from the wireless communication device, such as computers, printers, etc, (not shown).

As discussed above, the wireless communication device of the present invention includes a defibrillation module 24 within the device housing 56 and integrally connected to the control unit of the device for increased capability and compactness of the resulting wireless device. The defibrillator module may include a circuit (e.g. voltage converter, not shown) coupled to the power source that can convert the initial voltage available from the power source (110 Volts, batteries, etc) to a final voltage necessary to effectively treat an arrhythmic condition. The defibrillator is also in electrical communication with at least two electrodes 44 (FIG. 3). Upon activation of the defibrillator by the operator, the electrical charge is delivered to the victim via these electrodes. The electrodes are constructed and arranged on the outer surface of the wireless device to contact the victim's skin to deliver an electrical shock from the defibrillator in the device to the victim's heart.

As discussed above, the wireless device may also include a cardiac monitor 30 for monitoring the heart rhythm of the user. The cardiac monitor can be in communication with the same electrodes used to deliver the electrical shock from the defibrillator, as shown in FIG. 3. Otherwise, the cardiac monitor could include at least one additional sensing electrode (not shown) designed to monitor the user's heart beat.

For persons susceptible to heart arrhythmias, such as those patients who have recently undergone heart surgery or have chronic heart problems, it may be desirable to continuously wear electrodes which adhere to user's body and in electrical communication with the defibrillator and/or cardiac module inside the wireless device via any suitable conduction means (e.g., wires, wireless signals, etc.) that plug into corresponding electrical ports (not shown) located on the outside of the wireless device. These electrodes may be positioned diurnally by the wireless device user to predetermined locations on the body deemed adequate for electrically therapy and/or cardiac monitoring. In this situation, the wireless device should include a cardiac monitor which will detect cardiac arrhythmias and a defibrillator in fully automatic mode which will deliver the necessary electrical shock to the victim's chest when the cardiac monitor detects cardiac fibrillation. This embodiment is particularly suitable for persons not under constant medical supervision.

In a preferred embodiment a tracking device 48, such as, a Global Position System (GPS) unit is included inside the wireless communication device to provide the location of the wireless device in terms of longitude/latitude/altitude coordinates within the accuracy of the tracking system being used. For cellular phones, the tracking device may include any technology developed pursuant to the wireless 911 standard required by the U.S. Federal Communications Commission in which cellular phone service providers must provide the capability to locate a cellular phone handset. This includes time difference of arrival (TDOA) technology or timing advancement (TA) location measurement technology which tracks the strength, angle and arrival time difference of transmission signals from the cellular phone.

During operation, when the defibrillator module is initiated by the user, a signal will be sent to emergency personnel via the wireless service provider (FIG. 3) indicating that the patient has experienced a life threatening episode and that therapy is being delivered by the defibrillator. Emergency personnel (such as an ambulance) may be dispatched to provide assistance. Additionally, the tracking module will determine the location coordinates of the cellular phone handset and, if present, the microphone and speaker of the wireless handset are automatically activated for hands-free operation. The location coordinates may be then transferred to both the display of the phone so that the operator can communicate these coordinates to the emergency personnel via the transceiver to the emergency personnel 50. The wireless device will then prompt and guide the operator through the use procedures visually on the display, audibly through the speakers, or both.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system for providing immediate emergency assistance to a person experiencing cardiac distress, comprising:
   a handheld wireless communication device for sending and receiving communication signals, said wireless communication device including:
   a defibrillator module securable to said wireless communication device, said defibrillator module having an output coupled electrodes positionable on a person's chest, said defibrillator module having a power input being electrically connected to the output of a thermal battery, said thermal battery consisting of a pyrotechnic heat source formed from a cathode, an electrolyte, an anode and a collector, said thermal battery constructed and arranged to produce sufficient current to provide at least one electrical shock of an amp etude to treat a person in cardiac distress;
   means for activating thermal battery by said wireless device, means for activating said defibrillator by said wireless device, said wireless device contacting a service provider capable of receiving said communication signals indicating that said defibrillator has been activated and opening up a communication line with a first responder;

whereby said defibrillator provides an electrical shock to the person to reverse cardiac arrhythmia wherein said communication device provides two way communications with a first responder.

2. The system as set forth in claim 1, wherein said wireless communication device includes a cardiac module capable of detecting irregular cardiac arrhythmia within a patient's chest.

3. A handheld wireless communication device for sending and receiving communication signals during normal operation and capable of administering an electrical shock to a person experiencing cardiac distress, said wireless communication device comprising:

an automated defibrillator module for administering at least one electrical shock to the chest of a person to defibrillate the heart, said defibrillator module securable to said wireless communication device, said defibrillator module having an output coupled electrodes positionable on a person's chest, said defibrillator module having a power input being electrically connected to the output of a thermal battery, said thermal battery consisting of a pyrotechnic heat source formed from a cathode, an electrolyte, an anode and a collector, said thermal battery constructed and arranged to produce sufficient current to provide at least one electrical shock of an amp etude to treat a person in cardiac distress; and means for activating thermal battery by said wireless device, means for activating said defibrillator by said wireless device, said wireless device contacting a service provider capable of receiving said communication signals indicating that said defibrillator has been activated and opening up a communication line with a first responder;

whereby said communication device automatically opens communication with the first responder providing two way communications.

4. The wireless communication device as set forth in claim 3, further comprising a cardiac module capable of detecting irregular cardiac arrhythmia within said victim's chest.

5. The wireless communication device as set forth in claim 4, wherein said cardiac module includes at least one sensor capable of detecting cardiac arrhythmia, an output of said cardiac module is electrically coupled to a pair of electrodes.

6. The wireless communication device as set forth in claim 3, wherein said wireless communication device comprises a member selected from the group consisting of a cellular phone, satellite phone, pager, personal data assistant or a combination thereof.

7. The wireless communication device as set forth in claim 3, further comprising a tracking module for determining the location of the wireless communication device.

8. The wireless communication device as set forth in claim 7, wherein said tracking module is a global positioning system constructed and arranged to determine the location of said wireless communication device and transmit said location to a remote location.

9. The wireless communication device as set forth in claim 3, further comprising at least one multimedia device therein.

10. The wireless communication device as set forth in claim 3, wherein said thermal battery is sized and configured to be housed within the wireless communication device.

11. The wireless communication device as set forth in claim 3, wherein said thermal battery is formed as a power pack separate from the wireless device.

12. The wireless communication device as set forth in claim 3, further including an additional thermal battery that is formed as a power pack separate from the wireless device.

13. In combination with handheld cellular telephone capable of sending and receiving communication signals comprising:

a cardiac module capable of detecting irregular cardiac arrhythmia when in contact with a patient's chest, said cardiac module coupled to said telephone;

a defibrillator module for administering at least one electrical shock to the chest of said patient to defibrillated the heart, said defibrillator module being electrically connected to the output of a thermally powered battery consisting of a pyrotechnic heat source formed from a cathode, an electrolyte, an anode and a collector, said thermal battery constructed and arranged to produce sufficient current to provide at least one electrical shock of an amp etude to treat a person in cardiac distress and to said telephone;

means for activating thermal battery by said wireless device, means for activating said defibrillator by said wireless device, said wireless device contacting a service provider capable of receiving said communication signals indicating that said defibrillator has been activated and opening up a communication line with a first responder; and a tracking module capable of determining the location of the wireless communication device;

whereby said defibrillator is available to provide an electrical shock to the person to reverse cardiac arrhythmia if said cardiac module indicates a need for defibrillation wherein said communication device provides two way communication with a first responder include the location of the wireless communication to assist the first locator in rendering assistance.

* * * * *